United States Patent
Kersten et al.

(10) Patent No.: US 12,134,090 B2
(45) Date of Patent: Nov. 5, 2024

(54) REPURPOSING INFLATABLE PACKAGING PILLOWS AS BIOREACTORS: CONVENIENT SYNTHESIS OF GLUCOSONE BY WHOLE-CELL CATALYSIS UNDER OXYGEN

(71) Applicant: THE UNITED STATES OF AMERICA, AS REPRESENTED BY THE SECRETARY OF AGRICULTURE, Washington, DC (US)

(72) Inventors: Philip J. Kersten, Arena, WI (US); Thomas J. Schwartz, Orono, ME (US); James A. Dumesic, Verona, WI (US)

( * ) Notice: Subject to any disclaimer, the term of this patent is extended or adjusted under 35 U.S.C. 154(b) by 581 days.

(21) Appl. No.: 17/237,618

(22) Filed: Apr. 22, 2021

(65) Prior Publication Data
US 2021/0331131 A1 Oct. 28, 2021

Related U.S. Application Data

(60) Provisional application No. 63/013,592, filed on Apr. 22, 2020.

(51) Int. Cl.
*B01J 8/00* (2006.01)
*B01J 19/00* (2006.01)

(52) U.S. Cl.
CPC .......... *B01J 8/001* (2013.01); *B01J 19/0046* (2013.01)

(58) Field of Classification Search
None
See application file for complete search history.

(56) References Cited

U.S. PATENT DOCUMENTS 9,005,094 B2 * 4/2015 Little .................. B65D 31/145
493/213
2021/0331131 A1 * 10/2021 Kersten ............... B01J 19/0046

OTHER PUBLICATIONS

Gaab et al. (Chem. Eur. J., 2009, 15, 5450-5462).*
Ashraf (Process Engineer, Jun. 2023, 1-7).*

* cited by examiner

*Primary Examiner* — Hope A Robinson (57) ABSTRACT

A method of conducting oxidation in an inflatable bag bioreactor or a batch reactor is provided. The inflatable bag bioreactor or the batch reactor is used as an efficient, economical, and convenient reaction vessel. The inflatable bag bioreactor or batch reactor is rotated or rocked during the reaction to ensure continued exposure of the reaction mixture to the headspace gas in the vessel. The ability of the inflatable bag to expand or contract as the volume of the contents changes helps maintain consistent pressure and avoids the need to replenish the headspace gas.

15 Claims, 5 Drawing Sheets

REPURPOSING INFLATABLE PACKAGING PILLOWS AS BIOREACTORS: CONVENIENT SYNTHESIS OF GLUCOSONE BY WHOLE-CELL CATALYSIS UNDER OXYGEN

CROSS-REFERENCE TO RELATED APPLICATIONS

This application claims the benefit of U.S. Provisional Patent Application No. 63/013,592, filed on Apr. 22, 2020.

This invention was made with government support under 18-JV-11111126-044 awarded by the USDA/FS. The government has certain rights in the invention.

BACKGROUND

Biocatalysis (and chemical catalysis more generally) using molecular oxygen as the electron acceptor has shown significant potential for selective oxidation reactions attainable at a reasonable cost. However, oxygen is poorly soluble in water, and its slow rate of mass transfer in the aqueous phase is a major obstacle even for laboratory-scale syntheses let alone commercial scale processing. Oxygen transfer can be accelerated by vigorous mechanical methods, but these are often incompatible with biological catalysts and other components. More gentle conditions have been successful using shallow, high surface-area bag reactors that are designed for single-use and generally for specialized cell culture applications.

Molecular oxygen is considered the "greenest" oxidant in organic synthesis, and it has garnered increasing interest both in large industrial-scale syntheses and in fine chemical manufacture. Oxygen is abundant, inexpensive, and the product of its reduction ultimately is water, thereby decreasing environmental impacts and increasing atom efficiency in synthesis.

One challenge with using oxygen in a chemical synthesis is its limited solubility in solvents, particularly water. This limitation often leads to a reaction rate controlled by the rate of mass transfer of oxygen from the gas to the liquid phase rather than by the intrinsic kinetics of the chemical reaction. Chemical catalysis is also sometimes limited in its ability to achieve regio- and/or stereo-specificity. This shortcoming often precludes the use of oxygen in the manufacture of biologicals.

Oxygen-dependent enzymes provide an alternative to chemical catalysts and have potential advantages in achieving selective oxidations in an environmentally-sound manner. However, these reactions suffer the same reaction rate limitations associated with oxygen transfer from the gas to the liquid phase. Aggressive mechanical dispersive methods that may be used to increase oxygen transfer often tend to inactivate enzymes and whole-cell catalysts.

Whole-cell catalysis with POX (pyranose 2-oxidase) for the chemo-enzymatic synthesis of furylglycolic acid was previously reported. Schwartz T J, et al., "Integration of chemical and biological catalysis: Production of furylglycolic acid from glucose via cortalcerone", *ACS Catalysis* 2689-2693 (2013). A headspace consisting of pure oxygen is important for these reactions to compensate for the poor solubility of oxygen in water. However, if the reaction is carried out in a fixed-volume batch reactor with only an initial charge of oxygen, as would typically be done using a stoppered glass flask, the combination of high glucose concentrations coupled with small headspace volumes leads to a significant drop in partial pressure of oxygen as the reaction progresses. This decrease in partial pressure ultimately decreases the rate of mass transfer and, correspondingly, of the oxidation reaction.

This limitation can be ameliorated by repeatedly charging the headspace with oxygen, or by using a large headspace volume relative to the reaction volume to minimize the pressure drop. The inconvenience of both approaches is compounded by prolonged reaction times and parallel reactions. Continuous headspace exchange, such as with sparged stirred-tank reactors, is a costly alternative that can be technically challenging.

Thus, because of the low solubility of oxygen in water (e.g., 0.0013 mol/L for 1 bar of oxygen at 298° K), such approaches do not completely eliminate mass-transfer limitations, and measured reaction rates (or reaction selectivities) depend largely on aeration and agitation conditions that must be faithfully replicated in multiple batches to produce reliable, repeatable results.

Oxidation reactions with POX typically benefit from an oxygen or oxygen-rich environment, in combination with removal of peroxide produced from the oxygen during the reaction. High end bioreactors are often used, enabling the replenishment of oxygen and the effective removal of peroxide. However, such bioreactors typically are expensive to use.

As a result, reactor design to address these issues remains an active area of research.

SUMMARY

As an inexpensive but effective alternative to high-end bioreactors (and batch reactors more generally), the present process uses repurposed inflatable shipping or packaging pillows, or similar inflatable bags, which can include resealable valves to provide high-surface-area mixing between a liquid reaction mixture and a gas for preparative synthesis involving whole cells. Such inflatable packaging pillows, together with rotary shaking or rocking-motion-type incubators or stirrers to keep the contents well-mixed, provide and enable low-cost, preparative laboratory syntheses with biocatalysts (and chemical catalysts more generally), including under oxygen.

In one embodiment, the present subject matter relates to a method of performing a catalytic reaction using an inflatable bag as the reactor, the method comprising:
  (a) Inserting a liquid reaction mixture into an inflatable bag,
  (b) Inserting a suitable gas into a headspace of the inflatable bag, and
  (c) Permitting sufficient time for a catalytic reaction to proceed.

In another embodiment, the present subject matter relates to a method of performing biocatalysis using an inflatable bag as the bioreactor, the method comprising:
  (a) Inserting a liquid reaction mixture into an inflatable bag,
  (b) Inserting a suitable gas into a headspace of the inflatable bag, and
  (c) Permitting sufficient time for a biocatalytic reaction to proceed.

In yet another embodiment, the present subject matter relates to a method of conducting an oxidation reaction using an inflatable bag as the reactor, the method comprising:
  (a) Inserting a liquid reaction mixture into the inflatable bag, (b) Inserting an oxygen-containing gas into a headspace of the inflatable bag, (c) Rotating or rocking the inflatable bag while the oxidation reaction proceeds, and (d) Permitting sufficient time for the oxidation reaction to proceed.

Repurposing a shipping pillow or using a similar inflatable bag as a bioreactor (or a batch reactor more generally) is an elegant, easy, and economical approach. An inflater nozzle may be used to inflate the pillow under pressure through a valve in the pillow, such as an extended pillow valve. See FIGS. 2A, 2B. Upon removal of the nozzle from the valve, the valve reseals, for example when gentle pressure is applied (depending on the nature of the valve in use).

For use as a reactor or bioreactor, for example, the reaction liquid solution usually is first introduced into the uninflated pillow before the headspace oxygen or other gas. This step can be achieved, by way of non-limiting example, using a disposable Maxi Pipet Tip that may be cut at the narrow end for easy flow of liquid under gravity. In this embodiment, the pipette tip serves two functions: as a funnel to pour the liquid reaction mixture into the pillow; and as a spacer that separates the valve tube that extends into the bag from the sides of the uninflated pillow, so the liquid flows freely. Therefore, it is usually important to be sure that the pipette tip extends into the bag until it fits snuggly into the 3%-inch valve opening as liquid is poured into the pillow. Upon removal of the pipette tip from the valve, the valve opening is resealed, for example by gently pinching the valve.

At this point, the reaction medium will generally have been transferred into the pillow with little or no significant headspace because the liquid is introduced into a deflated pillow (generally supplied from the manufacturer without any gas in the pillow). Gas (air, oxygen, or any other desired composition) is introduced into the pillow under pressure, such as by way of non-limiting example using a fresh Maxi Pipet Tip as a nozzle (again, the narrow end may be cut to expand the opening into the pillow). Laboratory tubing, such as that sold under the C-Flex® trademark by Sigma Aldrich, may be used as an inflation hose. The inflation hose may have an outside diameter sized to fit snuggly inside the wide end of the pipette tip, allowing easy exchange of tips as needed. See FIG. 2A.

After inflation of the bioreactor (or the batch reactor more generally), the tip is removed from the pillow and again the valve is pinched to reseal the pillow. As a precaution, a clip (as is commonly used for dialysis bags) may be used as a secondary seal at the external valve extension. See FIG. 2B.

Once the liquid reaction mixture or medium and headspace gas are inserted into the pillow, suitable mixing of the contents generally is favorable to ensure continuous exposure of the reactants with the oxygen or other gas. For example, an incubator shaker may be used to rotate the bioreactor, thus causing the aqueous phase to travel up the sides of the pillow and facilitating surface area contact with the gas.

LIST OF ABBREVIATIONS

Pyranose 2-oxidase: POX
Glucose-methanol-choline: GMC
Carbohydrate Active enZymes: CAZy
Auxiliary active family 3: AA3
Nuclear magnetic resonance: NMR
D-arabino-1,4-lactone: AL
D-arabinonic acid: AA
Molded fiberglass: MFG
Terrific Broth (bacterial growth medium): TB
α-D-glucose: α-Glu
μ-D-glucose: μ-Glu
"Bag" and "pillow" bioreactors are used herein interchangeably.

DETAILED DESCRIPTION OF THE PREFERRED EMBODIMENTS

Inflatable, collapsible shipping pillows may serve as variable volume reactors—with the effective volume changing as the space within the pillow effectively expands or contracts as the reaction continues. This provides a convenient alternative to rigid-walled reactors, similar in some ways to the application of bag reactors in mammalian or insect cell culture. Further, not only do the pillows serve effectively to provide variable volume, but they also provide excellent results at significantly lower cost and with a simpler configuration, in part because headspace gas exchange is not required.

Bubble wrap has been used for analytical methods and to grow microorganisms. Here, inflatable shipping pillows are used as bioreactors that not only are economical but that also might circumvent issues related to the use of rigid-walled bioreactors.

One embodiment provides a method of performing biocatalysis using an inflatable bag as the reactor or bioreactor, the method comprising inserting a liquid reaction mixture into an inflatable bag, inserting a suitable gas into the headspace, or the otherwise unfilled area of the bag above the liquid reaction mixture, of the bag and permitting sufficient time for the reaction to proceed. Optionally the method includes rocking or rotating the inflatable bag bioreactor during the reaction.

Figure 2A:
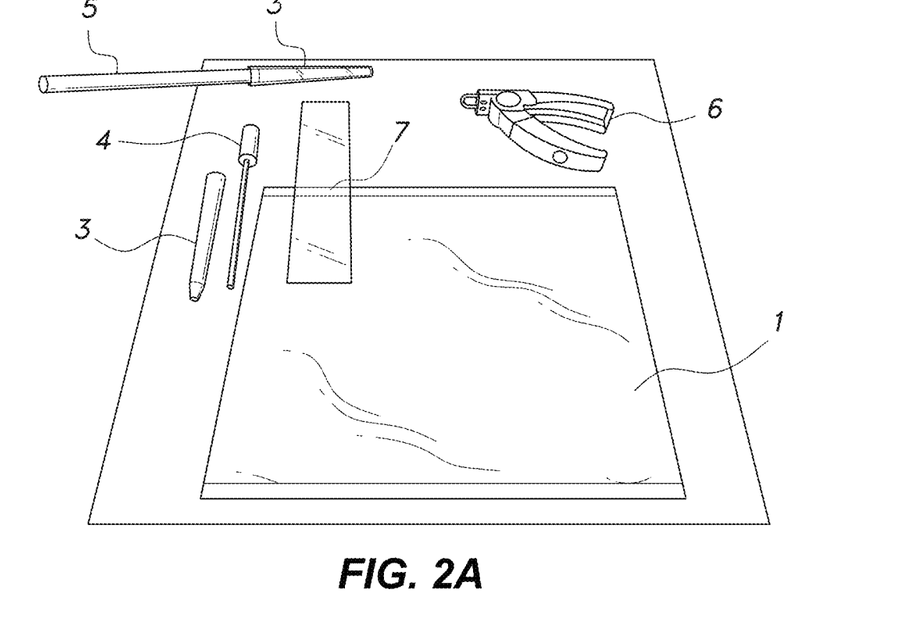
FIG. 2A shows a shipping pillow ready to be adapted as a reactor. The uninflated shipping pillow and accessories are shown. A 5-ml pipette tip with the narrow end clipped (using clippers shown upper right) may be used as a funnel once it is fully inserted through the resealable valve.

In particular, for example, the reaction liquid solution usually is first introduced into the pillow 1 before it is inflated with the headspace oxygen or other gas. This can be achieved, by way of non-limiting example, using a disposable pipette tip 3 that may be cut with clippers 6 at the narrow end of the pipette tip 3, for easy flow of liquid under gravity. The pipette tip 3 may serve two functions: as a funnel to pour the liquid reaction mixture into the pillow; and as a spacer that separates the walls of the valve for the entire length of the valve tube 7 that extends into the bag from the side of the uninflated pillow, so the liquid flows freely. Therefore, it is usually important to be sure that the pipette tip 3 extends into the bag 1 until it fits snuggly into the valve opening as the reaction liquid is poured into the pillow. The external extension of the valve can be shortened to facilitate placement of the pipette tip into the valve opening. Upon removal of the pipette tip 3 from the valve extension or valve tube 7, the valve opening is resealed, for example by gently pinching the valve at the edge of the pillow.

At this point, the reaction medium will generally have been transferred into the pillow with little or no significant headspace because the liquid is introduced into a deflated pillow (generally supplied from the manufacturer without any gas in the pillow). Gas (air, oxygen, or any other desired composition) is introduced into the pillow under pressure, such as by way of non-limiting example using a fresh pipette tip 3 as a nozzle (again, the narrow end may be cut, such as with clippers 6). Laboratory tubing, such as that sold under the C-Flex® trademark by Sigma Aldrich, may be used as an inflation hose 5. The inflation hose 5 may have an outside diameter sized to fit snuggly inside the wide end of the pipette tip, allowing easy exchange of tips as needed. See FIGS. 2A, 2B.

After inflation of the bioreactor (or the batch reactor more generally), the tip is removed from the pillow and again the valve is pinched to reseal the pillow. As a precaution, a valve clip 2 (as is commonly used for dialysis bags) may be used as a secondary seal at the external valve extension. See FIG. 2B.

Once the liquid reaction mixture or medium and headspace gas are inserted into the pillow, suitable mixing of the contents generally is favorable to ensure continuous exposure of the reactants with the oxygen or other gas. For example, an incubator shaker may be used to shake or rotate the reactor, thus causing the aqueous phase to travel up the sides of the pillow and facilitating surface area contact with the gas. During the reaction or after the reaction is completed, one or more samples of the reaction mixture may be removed using, for example, a transfer pipet 4.

Another embodiment provides a method of conducting an oxidation bioreaction, wherein the method comprises providing an inflatable bag, with a resealable valve, as a bioreactor; inserting a liquid reaction mixture into the inflatable bag; inserting a suitable gas into the headspace of the inflatable bag; rotating or rocking the inflatable bag while the oxidation bioreaction proceeds; and permitting sufficient time for the oxidation bioreaction to proceed. Optionally the method includes POX, present in the liquid reaction mixture, which is intended to oxidize glucose to produce glucosone.

One embodiment uses shipping pillows sold under the Fill-Air™ RF-1 mark and product label. This shipping pillow has a resealable valve designed for manual inflation with pressurized air. This valve can be used to introduce both a liquid reaction suspension and a defined headspace gas. See FIGS. 2A and 2B.

The desired properties for the bioreactor (or the batch reactor more generally) are typically:
1) high oxygen concentration in the headspace for extended reactions at, for example, high glucose concentrations using a single initial charge of oxygen;
2) high air-liquid interfacial area to facilitate oxygen transfer to the aqueous phase;
3) gentle mixing with no sparging or splashing to minimize cell and enzyme inactivation; and
4) simplicity of operation that would allow multiple experiments to be run in parallel at minimal cost in both expendables and equipment.

Figure 1:
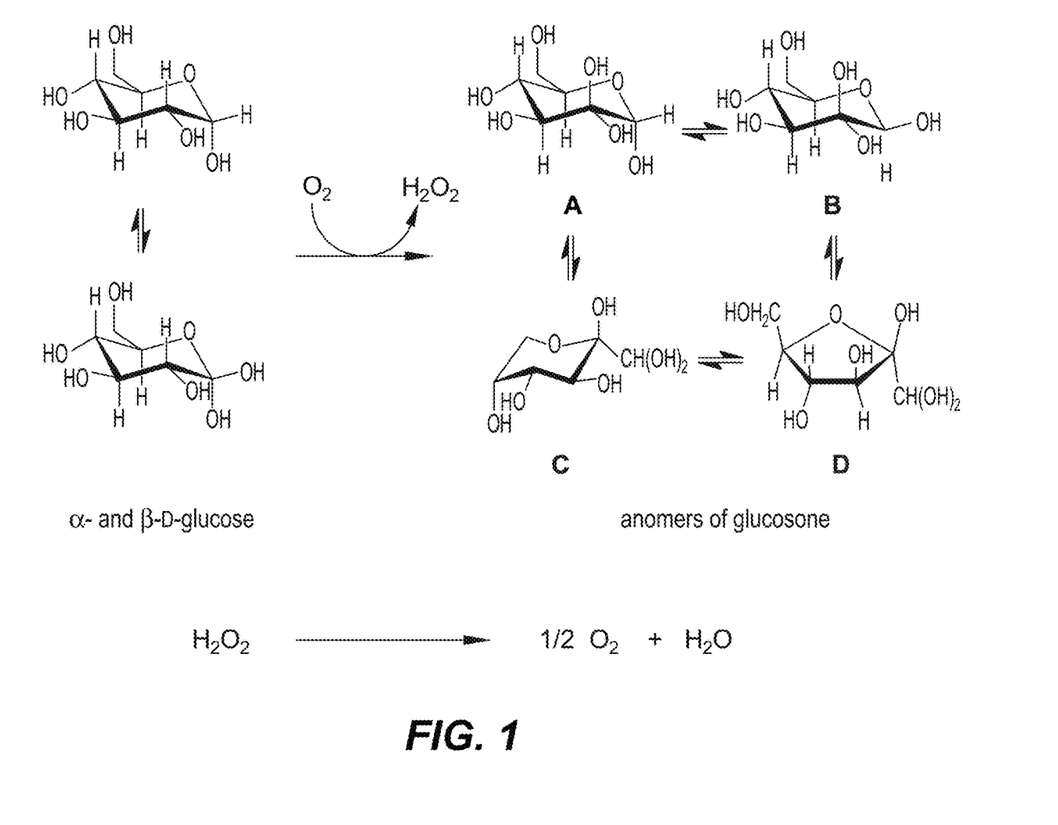
FIG. 1 depicts the reaction scheme for oxidation of both α- and β-D-glucose at C-2 by POX (pyranose 2-oxidase) to produce glucosone and peroxide (upper equation). The glucosone equilibrates as four isomers (more specifically, anomers) in water, labeled as A, B, C, and D. Catalase converts peroxide to oxygen and water (lower equation).

In one embodiment, procedures to repurpose the shipping pillow as a bioreactor are described here for the oxygen-dependent conversion of glucose to glucosone catalyzed by pyranose 2-oxidase (POX) from *P. chrysosporium* expressed in *Escherichia coli*. See FIG. 1. Of course, these methods have broad application to other oxidizing enzymes and to whole-cell catalysts.

For example, pyranose 2-oxidases (POXs) are useful for the oxidation not only of glucose but also of related sugars for the synthesis of rare keto sugars and fine chemical synthons. Glucosone has been applied in the enzymatic and chemo-enzymatic synthesis of fructose and in the chemo-enzymatic synthesis of furylglycolic acid. Fungal pyranose 2-oxidases (POXs, also designated Enzyme Commission number EC 1.1.3.10) are members of the functionally diverse glucose-methanol-choline (GMC) superfamily and are proposed to play a role in lignocellulose metabolism by supplying peroxide for peroxide-dependent enzymes. These oxidases comprise, along with other fungal GMC enzymes, the auxiliary activities family AA3 of the CAZy database of carbohydrate-active enzymes, with POX included in (sub) family AA3_4.

Pyranose 2-oxidases are found in diverse basidiomycetous fungi, and a subset of these fungi also express pyranosone dehydratase, which converts glucosone to cortalcerone—thought to function as an antibacterial agent suppressing competition for wood decay fungi. In addition to decay wood basidiomycetes, POX has also been characterized from ascomycetes and bacteria. Therefore, there is a broader context of possible use of POX catalysts for sugar oxidations with molecular oxygen.

In one embodiment, the pillow bioreactors may be used to synthesize glucosone from glucose on a multi-gram scale with molecular oxygen as the two-electron acceptor for oxidation of the glucose, and with pyranose 2-oxidase (POX) as the regio-selective catalyst. See Figure. 1. The reactions may be catalyzed by POX and catalase, wherein the POX catalyzes the oxidation of glucose to glucosone, and the catalase catalyzes the decomposition of hydrogen peroxide to water and oxygen. Both α- and μ-D-glucose are oxidized at C-2 by POX to produce glucosone and peroxide (upper equation in FIG. 1). The glucosone equilibrates as four isomers in water. See FIG. 1. The peroxide that is produced is deleterious to the POX reaction, and so may be consumed using catalase (lower equation in FIG. 1).

One study focuses on *E. coli* whole-cell catalysis with recombinant POX from the white-rot wood decay fungus *Phanerochaete chrysosporium*. The corresponding POX cDNA from this basidiomycete codes for 621 amino acids and the recombinant protein includes an N-terminal T7-epitope and C-terminal hexahistidine tag. The 270-kDa oxidase is homotetrameric and consists of four identical 68-kDa subunits, each with a flavin adenine dinucleotide active site.

In another embodiment, the reactor may be used for synthesis of glucosone (D-arabino-hexos-2-ulose) from D-glucose using *Escherichia coli* whole cells expressing recombinant pyranose 2-oxidase (POX) as catalyst. Parallel reactions may be performed for systematic study of the effects of headspace composition (i.e., air vs 100% oxygen), cell density, exogenous catalase, and reaction volume in the oxidation of 10% glucose. Importantly, at a high concentration of substrate only a single charge of 100% oxygen is typically required for complete conversion of 10% glucose in 18 hours, thus economizing both on pure oxygen as a reagent and on the equipment that would otherwise be necessary if the headspace needed instead to be continually exchanged.

In another embodiment, a support for the pillow may be made, for example, of thermoplastic material sold under the trademark Kydex® V. When placed in a close-fitting container the support may be adjusted or fitted so as to prevent the reactor from independently rocking, helping to maintain a parabolic surface for the reaction solution. However, even with such a pillow support the mixing characteristics of the system may change as the reaction progresses and the bag deflates. Additional effort may be required to maintain more consistent mixing patterns (such as, for example, application of pressure to the bag).

One embodiment may use, for example, a rotational mixer at a frequency of 100 rpm or otherwise, with the aim being, for example, to maximize travel of the solution up the sides of the reactor under the initial reaction conditions.

Figure 2B:
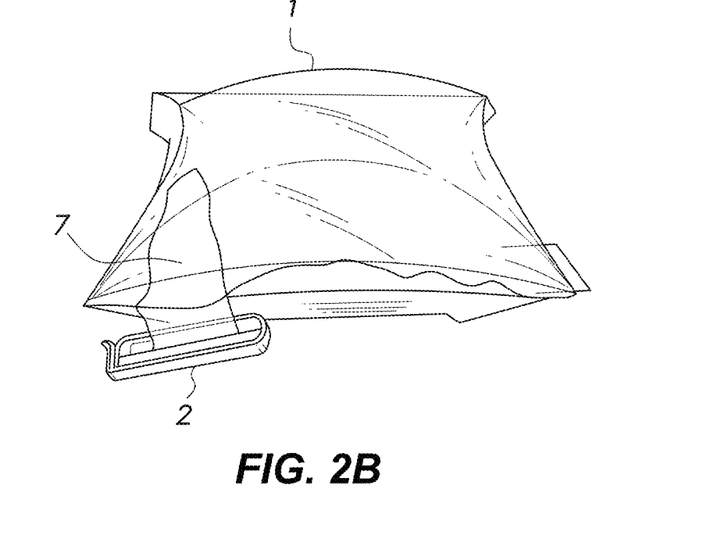
FIG. 2B shows the inflated pillow after addition of the liquid reaction suspension and the headspace air, oxygen, or other suitable gas.

For single-time point evaluation of the bioreactor contents, a corner of the bioreactor may be cut to allow removal of the contents. For time-course studies, samples may be removed through the valve with a transfer pipet 4, shown immediately left of the shipping pillow in FIG. 2A. In FIG. 2B is shown an inflated pillow containing 50 ml of water, for demonstration, in a support made of thermoplastic material. The valve clip 2 on the external valve extension 7 is used as a precaution against leaks.

EXAMPLES

Example 1—Glucose Consumption and Glucosone Production

Figure 3A:
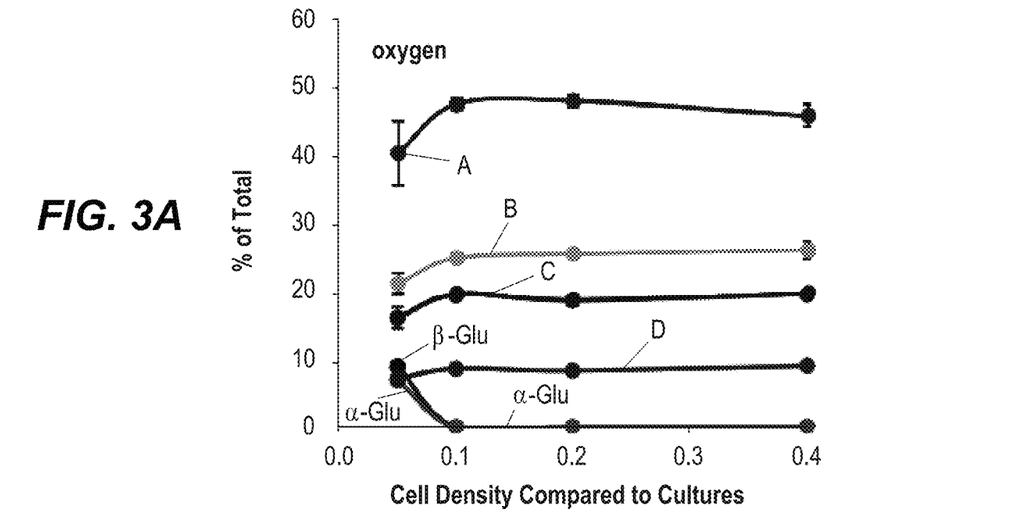
FIG. 3A shows glucose consumption and glucosone production as a function of POX cell density, using oxygen as the headspace gas. The separate glucosone isomers are labeled A, B, C, and D.
Figure 3B:
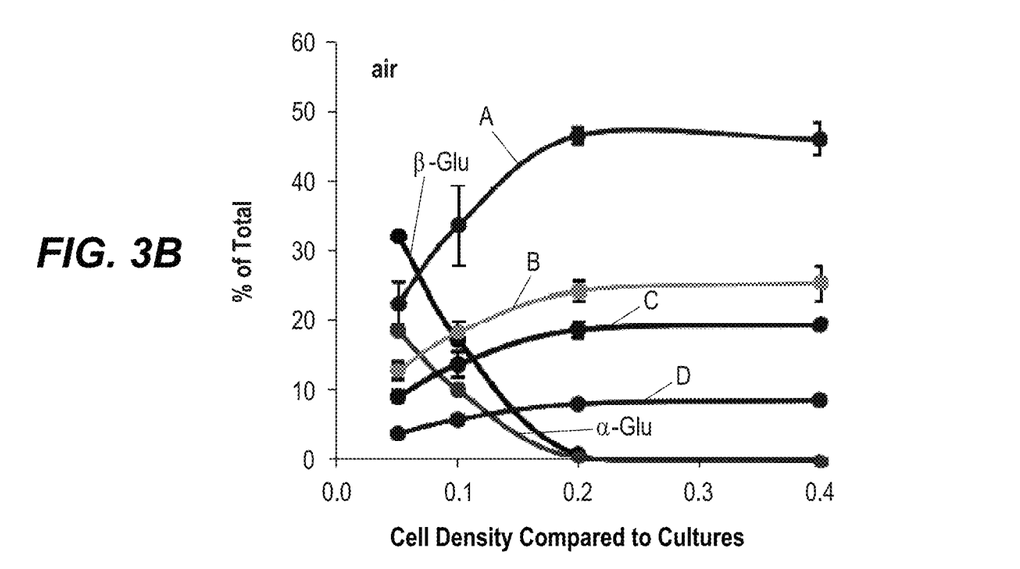
FIG. 3B shows glucose consumption and glucosone production as a function of POX cell density, using air as the headspace gas. The separate glucosone isomers are labeled A, B, C, and D.

Glucose consumption and glucosone production may be determined as a function of POX cell density. Multiple reactions may be run at various cell densities, for example comparing results with oxygen or air headspace. See FIGS. 3A and 3B. The α-D-glucose (α-Glu), μ-D-glucose (β-Glu) and glucosone anomers reflected in FIGS. 3A and 3B (see FIG. 1 for anomer letter designations) were quantified by NMR spectroscopy. Cell densities depicted in FIGS. 3A and 3B are with respect to the time of harvest. The catalase concentration was 50 μg/ml.

Figure 4A:
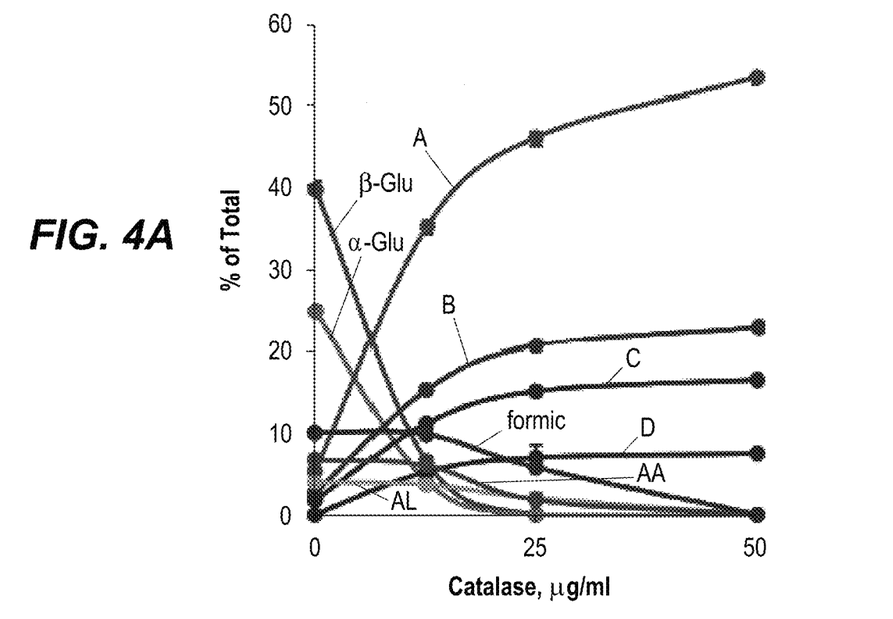
FIG. 4A shows glucose consumption and glucosone formation as a function of catalase amount present, depicting the anomeric complexity of glucose and glucosone and the side products of formic acid, D-arabino-1,4-lactone (AL) and D-arabinonic acid (AA) in 18-h reactions as a function of catalase concentration. The separate glucosone isomers are labeled A, B, C, and D.
Figure 4B:
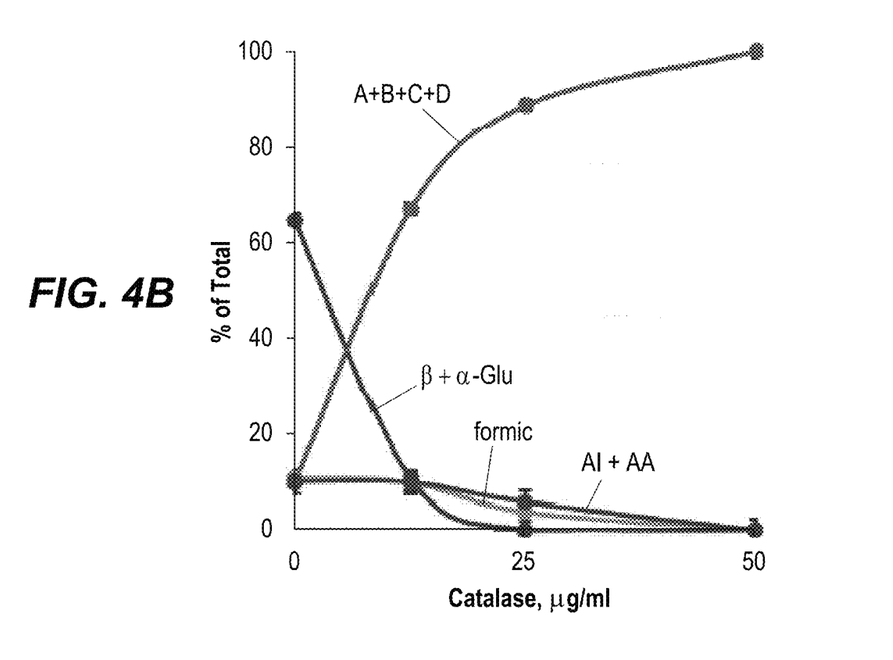
FIG. 4B shows glucose consumption and glucosone formation as a function of catalase amount present, depicting amounts of glucose anomers, glucosone anomers, formic acid, and (AL+AA) as a function of catalase concentration. The glucosone isomers are labeled jointly as A+B+C+D.
Figure 5:
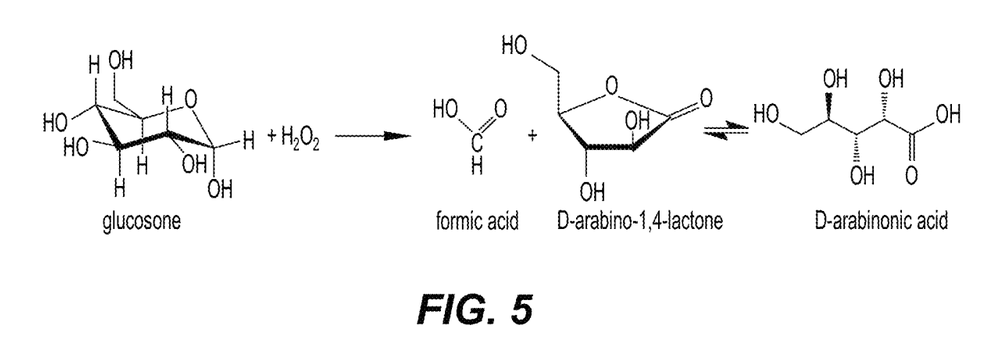
FIG. 5 shows the resulting near equimolar amounts of formic acid and (AL+AA) formed at low catalase concentrations from glucosone and hydrogen peroxide, as reflected in FIGS. 4A and 4B.

FIGS. 4A and 4B show glucose consumption and product formation as a function of catalase concentration. FIG. 4A shows the anomeric complexity of glucose and glucosone and the side products of formic acid, D-arabino-1,4-lactone (AL) and D-arabinonic acid (AA) in 18-h reactions. FIG. 4B shows amounts of glucose anomers, glucosone anomers, formic acid, and (AL+AA). Results indicate near equimolar amounts of formic acid and (AL+AA) are formed at low catalase concentrations, supporting evidence for their formation according to the equation of FIG. 5, which reflects a proposed mechanism for side-product formation in the absence of exogenous catalase. With no addition of catalase, there was approximately 5% unidentified product(s) that were not accounted for in these graphs. The production of formic acid, D-arabino-1,4-lactone and arabinonic acid can be explained by the reaction of glucosone with hydrogen peroxide.

Example 2—Time Course Reaction

Figure 6:
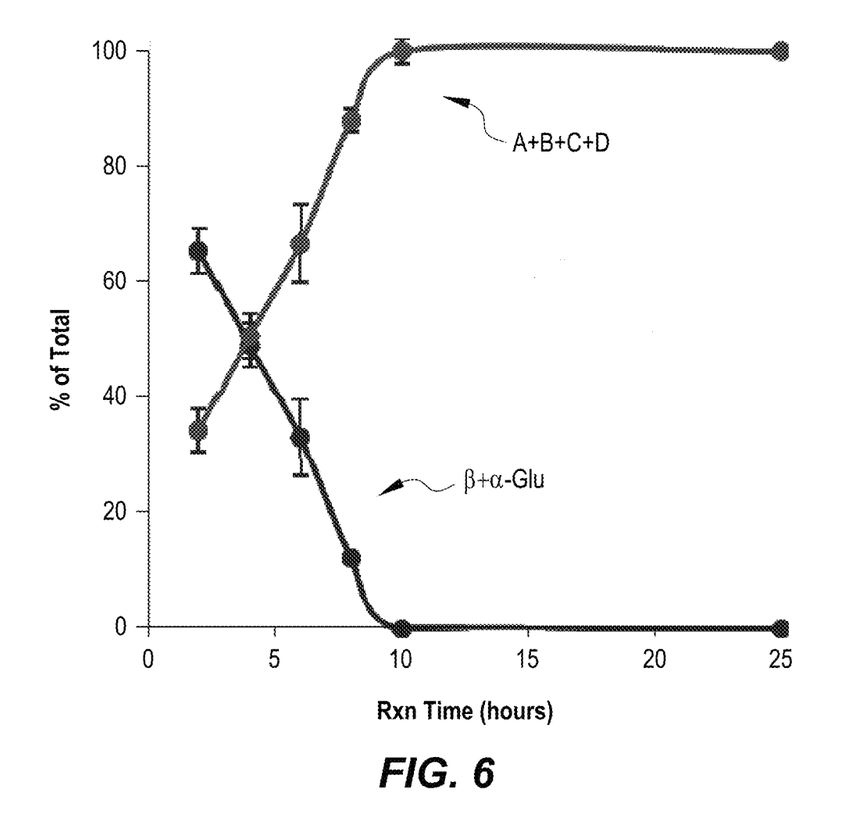
FIG. 6 plots the time course reaction at 200-ml scale under oxygen, depicting the growing presence of glucosone isomers and decreasing presence of glucose.

FIG. 6 reflects a time course reaction at a 200-ml scale under oxygen. The concentrations of glucose and glucosone were determined over time by NMR, in samples removed from the 200-ml reaction mixture through the resealable valve with a transfer pipet. The reactions were run in triplicate.

Example 3—Preliminary Studies

For comparison regarding prior glucose concentration and incubation time for reactions, we considered earlier results where complete conversion of glucose was achieved at a gram-scale or higher. One early study with immobilized pyranose 2-oxidase from *Polyporus obtusus* demonstrated complete conversion of 2 g/L glucose in 24 h under air. More recent work reports complete conversion of 1 g/20 ml (i.e., 5% w/v) glucose with pyranose oxidase from *Trametes hirsute* in 24 hours under air. Another study observed complete reaction for 200 ml of 250 mM glucose in only 5 hours with POX from *Trametes multicolor* when pure oxygen was supplied through a sintered glass tube. The report of the highest glucose concentration we found, as well as the longest incubation time, was in a roller mixer with 5 g of glucose dissolved in 20 ml water, incubated for 48 hours with aeration of the solution using compressed air every hour for 3 minutes.

Example 4—Comparative Reaction

Based on these earlier results reflected in Example 3, and the desire that the reactions should proceed unattended, we performed the reaction with 18-hour (overnight) incubation times and an initial glucose concentration of 10% glucose (i.e., 555 mM). In contrast to the earlier studies which used purified pyranose 2-oxidases, we used whole-cell catalysis with *E. coli* producing intracellular pyranose 2-oxidase from *P. chrysosporium*. This example describes the methods used herein.

Methods

Materials. Catalase purified from bovine liver and D-Arabino-1,4-lactone were purchased from Sigma-Aldrich. Fill-Air™ brand RF-1 inflatable packaging pillows produced by the Sealed Air® company were purchased from Uline (model S-5234; 9×11 inches, 0.2 cu. ft). Maxi Pipet Tips (#21-195-3; 1000-5000 ul), transfer pipets (#13-711-GM)

and molded fiberglass trays (MFG Tray, Linesville, PA; model #920108; 29.84×22.22×10.41 cm; Fisher Scientific catalog #15-239-33) were purchased from Fisher Scientific. Tubing sold under the C-Flex® mark (#SK-06424-74; ¼"1 D×½"OD) was purchased from Cole-Parmer®. Thermoplastic sold under the Kydex® V mark (0.060" Thick-12"× 12"; manufactured by Sekisui SPI) was purchased through Amazon.com. Plaster cloth gauze was purchased from a local hobby shop.

Preparation of bioreactor supports. A fully inflated Fill-Air™ RF-1 pillow requires a support so as to allow the pillow to move in coordination with the incubator shaker, as opposed to rocking in place. Supports were made by first making a cast of an inflated pillow with plaster gauze (the cast is made to half of the inflated pillow), then the cast was used to make pillow supports from the Kydex® V brand thermoplastic. Eight tapered notches, about 3 inches long and 1 inch wide at the edge of the sheet, were cut into the 12×12-inch thermoplastic sheets in a radial pattern to help the thermoplastic sheet conform to the shape of the cast without buckling. The notched thermoplastic sheets were then preheated at approximately 170° C. until pliable, and then pressed into the plaster cast supported in a bed of sand. The formed sheet was then trimmed using shears, and the shape fine-tuned using a heat gun so that the formed sheet would fit in the MFG tray.

Bacterial Strain and Plasmids.

The cDNA sequence (GenBank accession number AY522922) encoding POX of *P. chrysosporium* BKMF-1767, with an N-terminal T7-tag and a C-terminal His6-tag, was synthesized for optimized expression in *E. coli* and inserted in a pJ414 plasmid (ATUM, Newark, California, USA). A control pJ414 plasmid with no opening reading frame in the insert was also prepared and both plasmids transformed into BL21(DE3) *E. coli*.

Growth and Preparation of Cells for Catalysis.

Cultures were grown overnight on non-inducing medium to inoculate auto-induction medium. Each liter of auto-induction medium contained: 48 g Terrific Broth (TB) powder, 2 mM $MgSO_4$, 0.2X Trace Metals (1000X Trace metals, Teknova Cat. No: T1001), 28 mM disodium succinate, 0.005% Antifoam 204, 16 g glycerol, 0.3 g glucose, and 10 g lactose. The glycerol, glucose and lactose were autoclaved separately before being added to the medium. Filter-sterilized carbenicillin (100 µg/ml final concentration) provided selection. Five hundred ml of auto-induction medium in 2-L baffled flasks was inoculated with 3 ml of non-induced culture and incubated at 250 rpm, 20° C. for 30 hours. Cells were harvested as 40-ml aliquots in 50-ml conical centrifuge tubes at 4000× g for 15 minutes. The supernatants were removed, and the cell pellets overlaid with 10 mM citrate pH 6 buffer before storage at −20° C.

Reaction Conditions.

The reactions were conducted at 10% glucose in 10 mM pH 6 sodium citrate. Catalase was added. A fiberglass tray was used to contain the repurposed Fill-Air™ RF-1 brand bioreactors with or without a Kydex® V brand thermoplastic support. Incubation was conducted at 100 rpm and 22° C. using standard laboratory incubators with a 1" rotational diameter. A corner of the bioreactor was cut to release the contents, or a transfer pipet 4 used to remove samples for time-course experiments. See FIG. 2A.

To prepare the BL21(DE3) *E. coli* cells for catalysis, the 50-ml centrifuge tubes with frozen pellets and overlays were centrifuged to maintain the cell pellets as the overlays thawed (about 15 minutes) and the supernatants discarded. The cell pellets were then washed twice by suspending each pellet in 40 ml of 10 mM pH 6 sodium citrate and centrifuging at 4000× g for 15 minutes and the supernatants discarded.

Enzyme Assays.

POX activity in the cell extract was determined in a peroxidase-coupled assay, where one unit of POX is defined as the amount of enzyme required to oxidize 1 µmol of glucose per minute. To prepare *E. coli* cell extract for the determination of POX activity, a cell pellet (approximately 2.2 g wet weight) from 40 ml of culture was sonicated (Qsonica Model Q700) in 10 ml of 50 mM Tris pH 8, 50 mM NaCl, 5% Glycerol for a total processing time of 20 minutes, and the sonicate was then centrifuged. Based on the assay of the cell extract, the POX activity was estimated to be 4,500 U/L of culture, comparable to the previous report of POX activity in cultures of BL21(DE3) *E. coli* transformed with pox in pET21a(+).

Catalase activity was determined at 240 nm in 50 mM Tris-HCl buffer (pH 9.0) using 10 mM $H_2O_2$ and an extinction coefficient for $H_2O_2$ of 39.4 $M^{-1}$ $cm^{-1}$. One unit of catalase is defined as the amount of enzyme required to decompose 1 µmol of peroxide per minute. The specific activity of the catalase in our studies was 3,800 U per mg protein.

NMR Spectroscopy.

NMR experiments were run on a Bruker Avance III HD 500 MHz instrument fitted with a 5-mm Prodigy triple resonance inverse-detection TCI cryoprobe with z-gradients. The quantitative $^{13}$C-NMR analyses used the standard Bruker pulse program with an inverse-gated proton-decoupling sequence, a 30° pulse angle (4 µs) and a 90 s relaxation delay. Spectra were recorded with 64k data points and a 236 ppm spectral window. Exponential multiplication (LB=I.0) and one level of zero-filling was performed prior to Fourier transformation. All samples were run in $H_2O$: $D_2O$ mixture and spectra were referenced using the Bruker default solvent table with no reference shift for $D_2O$. Peaks were picked using the automatic routine and a minimum intensity of 0 and a peak detection sensitivity of 1.40.

NMR Data Analysis.

Peak tables were exported to Excel for comparison of peak heights. For each component in a particular sample, peak heights of the non-overlapping carbon signals were totaled, then divided by that number of carbons to obtain the relative ratio of components. The relative ratios were scaled so that their total was 100 and then graphed as a percentage of total. The chemical shift assignments for glucosone were based on reported values.

Example 5

Cells from frozen pellets were washed twice with 10 mM citrate prior to reaction with glucose for the following reasons:
 1) to remove components of the rich growth medium,
 2) washing may improve permeability particularly when a rich growth medium is used, and
 3) to remove loosely bound metals as citrate complexes that may contribute to Fenton-type reactions in the presence of peroxide generated by POX.

Experiments were conducted at the 50-ml reaction scale using cells harvested from 40 ml of culture, or a cell density of 0.8 in reference to cultures at time of harvest. The cells corresponding to 40 ml culture had a wet weight of approximately 2.2 g and activity of 190 U as determined by assaying supernatants of sonicated cells, as described above. In our earlier syntheses of glucosone by whole-cell catalysis in Erlenmeyer flasks we used catalase at 50 µg/ml reaction solution.

We then tested catalase levels at 50 µg/ml and at 100 µg/ml to determine if sufficient catalase was being used to protect the whole-cell catalysis in 18-hour incubations with a headspace of 100% oxygen. Reactions in triplicate at both catalase levels were completed as determined by quantitative NMR, which requires assignment of all the anomeric species as reflected in FIG. 1. Based on these studies, we continued to test the response to cell density and headspace composition at a constant catalase concentration of 50 µg/ml reaction.

Example 6—Reaction as a Function of Cell Density, Headspace Composition (Oxygen Vs Air)

A series of pillow reactions with 50 ml of 10% glucose were run in triplicate with two-fold serial dilutions of cells, the catalase concentration at 50 µg/ml, and with the headspace filled with either 100% oxygen or air. Reactions were harvested at 18 hours and samples were analyzed by quantitative NMR. See FIGS. 3A and 3B. Surprisingly, reactions were completed in 18 hours even with only 0.1 cell density (compared to growth culture cell density) under oxygen and with 0.2 cell density under air.

The bioreactor in this simple arrangement is a closed system and has a single charge of headspace at the beginning of the reaction. Accordingly, the stoichiometry of the reaction is an important consideration. See FIG. 1. For example, in the 50-ml reaction volumes with 10% glucose, there are 0.028 moles of glucose requiring 0.028 moles of oxygen. However, the dismutation of the peroxide by catalase generates oxygen. The 0.028 moles of oxygen consumed generates 0.028 moles of peroxide which dismutates to provide 0.014 oxygen. See the lower equation of FIG. 1. Accordingly, a minimum of 0.014 moles of oxygen must be provided in the headspace to achieve oxidation of 5 grams of glucose to glucosone in a coupled-reaction with catalase.

The pillow has a nominal volume of 5.6 L (0.2 $ft^3$), but the measured displacement volume of a fully inflated pillow is only about 3.2 L. Therefore, the headspace in a pillow inflated with oxygen contains approximately 0.13 moles (assuming an ideal gas at 1 atm)—an approximately tenfold excess compared to the minimum amount of oxygen required by stoichiometry. Because the pillow is not a rigid vessel, the total pressure in the system remains at approximately 1 atm throughout the reaction.

Assuming that the gas exchange across the low-density polyethylene bioreactor surface is negligible over the 18-hour reaction time (which is reasonable, given that typical diffusivities of oxygen across LDPE (low density polyethylene) membranes are on the order of $1 \times 10^{-7}$ $cm^2/s$), the bioreactors with 100% oxygen should maintain a headspace of about 100% oxygen at approximately 1 atmosphere throughout the reaction. Conversely, if the pillow were inflated with air (21% oxygen), then the pillow bioreactor will hold 0.027 moles of oxygen, which is still a twofold excess of that required for complete conversion of 5 g of glucose. However, despite the constant total pressure ensured by the pillow vessel, the oxygen composition of an air headspace will decline from 21% to about 10% oxygen during the course of the reaction, which leads to a decrease in the partial pressure of oxygen and thus a decrease in the oxidation rate as the reactions progress. See FIGS. 3A and 3B.

Example 7—Reactions as a Function of Catalase

The role of catalase in these reactions was tested using a cell density of 0.2 because this provided sufficient cells (about 2 times that required for an 18-hour reaction) for complete conversion of glucose under oxygen. See FIG. 3A. Using a two-fold series of dilutions of catalase, a strong dependence on catalase for completion of reactions was demonstrated. See FIGS. 4A and 4B. Importantly, reactions with no exogenous catalase showed significant levels of D-arabino-1,4-lactone, D-arabinonic acid, and formic acid. See FIG. 5.

Control reactions with 10% glucose and whole cells prepared in the same manner, except with pJ414 plasmid with no open reading frame, showed no conversion of glucose in the presence of catalase at 50 µg/ml reaction solution. The result showed that pyranose 2-oxidase is required for conversion of glucose to glucosone, and that catalase has a strong influence on the extent of the reaction, presumably by preventing inactivation of pyranose 2-oxidase.

The reaction of glucosone with peroxide to form D-arabino-1,4-lactone, D-arabinonic acid, and formic acid (see FIG. 5) has been suggested previously. Cleavage of glucosone has been demonstrated to be first-order with respect to hydrogen peroxide and hydroxyl ion at low alkalinities. Under the mildly acidic starting conditions (pH 6) of the reactions here, this non-enzymatic reaction may have occurred subsequent to significant accumulation of peroxide, thus delaying the drop in pH associated with formic acid and D-arabinonic acid production that would be expected to inactivate enzymatic catalysis. Detailed kinetic studies may help to disentangle the possible reaction pathways, including time-dependent changes in post-harvest samples.

Example 8—Increased Reaction Scale Under Oxygen and Air

Based on the analyses discussed above on available oxygen in the pillow reactors and the stoichiometry of the reactions, it seemed plausible that reactions under pure oxygen could be scaled successfully to 200 ml, but whether the reactions would be complete in 18 hours was uncertain. Reactions run in triplicate for 18 hours under oxygen and air showed that the reactions under oxygen were completed in that time, whereas the reactions under air were a little less than half complete. This is consistent with oxygen being the limiting reactant under air. Recognizing that reactions could be scaled to 200 ml under oxygen, but that the quality of mixing quickly degraded as the bags deflated even with use of the thermoplastic supports, we tested 200-ml reactions under oxygen but without supports. As expected, the bags without form-fitted support rolled around the rectangular molded fiberglass containers in the rotary incubator. However, as the oxygen is consumed, the bags flatten, the reactors stabilize, and the mixing becomes more consistent.

As a further test of the utility of the process, cells were recovered by centrifugation and reused in fresh solutions of 10% glucose and catalase. Complete conversion of glucose was observed for an 18-h reaction. We did not determinate how many cycles the cells can be reused, but factors such as the efficiency of cell recovery from the high surface area bioreactors, and susceptibility of cell walls to freeze-thaw cycles, likely would be important.

A time course study of 200-ml reactions with no form-fitted support showed the reactions to be complete in 10 hours. See FIG. 6. Importantly, samples could be removed through the resealable valve without significant deflation of the pillows, and no oxygen was replenished to the pillows for the entire time course and yet the reactions proceeded to completion. Based on these conditions (0.2 L reaction volume, 10% glucose, completion in 10 hours), a volumetric productivity of 9 g/(L·h) is observed, which is remarkably similar to that observed with purified POX from *T. multicolor* in a continuously stirred reactor (200 rev/min) with sparging oxygen through a sintered glass tube. Likewise, the reactions here (FIG. 6) used approximately 1 U POX/ml reaction (based on estimation of sonicated extract) and provides a specific productivity of 9 mg/(L·h·U POX) which is also similar to that observed with the reactor using purified POX.

Detailed comparisons have limitations in that these are not kinetics studies, and in one case whole cells are used while in the other a homogeneous catalyst (i.e. POX). In addition, the sources of the two POX enzymes are not the same and the reported kinetics have substantial differences. For example, the $K_m$ for oxygen with POX from *P. chrysosporium* is 1.2 mM while that for *T. multicolor* is 0.09 mM. On this basis we might expect the system with *P. chrysosporium* to be more responsive to oxygen concentration over the dynamic range achieved with an oxygen headspace, but at perhaps a lower catalytic efficiency and in the presence of an additional diffusion barrier, i.e., the bacterial cell wall.

CONCLUSIONS

These results demonstrate the effective, convenient, and economical approach in using a disposable pillow reactor that requires only a single charge of headspace for whole cell catalysis. These benefits may be the determining factor for the scale of a research study.

For example, it is intuitive that whole cell catalysis (when it is an option) is much simpler than homogeneous catalysis requiring cell lysis and enzyme purification with additional time and resources. Also, an inflated pillow reactor with no attachments is significantly easier to prepare than a stirred sparged reactor with electrical connections (for the stirring motor) and gas connections (for sparging).

With the pillow reactors used in this study, four reactors can be easily accommodated in a rotary incubator with a 30×18 inch platform. With 3 incubators available, 12 parallel reactions are easily accommodated providing 3 replicates under 4 different reaction conditions (see FIGS. 3, 4A, and 4B). In the case of stirred-tank sparged reactors, the logistics of supplying continuous gas flow to similar multiple parallel reactions would be daunting. In the case of pillow reactions containing 200-mls solution and approximately 3 L headspace, about 150 ml of oxygen per gram of glucose is provided, whereas in a continuous flow system, about 20 times that amount of oxygen is delivered at 0.1 L/min.

Recognizing that a rotational mode of mixing is not the only option, we performed preliminary experiments using 200-ml reactions but with the bioreactor only partially inflated with 100% oxygen so that it is stable on a flat surface and allows consistent mixing on a rocking-motion-type incubator without need for a form-fitted support. This configuration also leads to complete conversion of 10% glucose in 18 hours. This mode of mixing is more closely related to the wave-induced mixing used in previous reports.

Use of inflatable packaging pillows with resealable ports provides convenient, inexpensive and effective bioreactors. Incubators commonly found in laboratories, such as rotary shaking or rocking-motion-type, are suitable for providing mixing with minor modifications. The utility of the bioreactor bag is exemplified with the overnight synthesis of glucosone under oxygen, leading to essentially quantitative yields of glucosone using whole-cell catalysis. The facility of the process may open the door to future studies with more complex systems, such as chemo-enzymatic reactions.

It is to be understood that the new methods and apparatus described here are not limited to the specific embodiments described above, but instead encompass any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of performing catalysis having an inflatable bag for a reactor, the method comprising:
    (a) inserting a liquid reaction mixture into an inflatable bag, wherein the inflatable bag is an inflatable packaging pillow with a resealable valve;
    (b) inserting a suitable gas into a headspace of the inflatable bag; and
    (c) permitting sufficient time for a catalytic reaction to proceed, wherein an incubator shaker is attached to the inflatable bag to provide rotation or rocking of the inflatable bag while the reaction proceeds.

2. The method of claim 1, wherein the catalytic reaction is a bioreaction.

3. The method of claim 2, wherein the inflatable bag is an inflatable packaging pillow.

4. The method of claim 1, wherein the catalytic reaction is a bioreaction, and the biocatalysis comprises oxidation.

5. The method of claim 4, wherein the suitable gas is oxygen.

6. The method of claim 2, wherein the inflatable bag is a disposable bag intended for one use.

7. The method of claim 6, wherein an incubator shaker is attached to the inflatable bag to provide rotation or rocking of the bag while the reaction proceeds.

8. The method of claim 5, wherein the liquid reaction mixture comprises pyranose 2-oxidase.

9. The method of claim 8, wherein the method is used to oxidize glucose.

10. The method of claim 9, wherein the method is used to produce glucosone.

11. The method of claim 4, wherein the inflatable bag is rotated or rocked while the reaction proceeds, and wherein the method is used to oxidize glucose and produce glucosone.

12. The method of claim 11, wherein one or more portions of the liquid reaction mixture are removed from the inflatable bag before the reaction is completed.

13. The method of claim 5, wherein one or more portions of the liquid reaction mixture are removed from the inflatable bag before the reaction is completed.

14. The method of claim 5, wherein the reaction is completed before any of the liquid reaction mixture is removed from the inflatable bag.

15. A method of performing catalysis having an inflatable bag for a reactor, the method comprising:
    (a) inserting a liquid reaction mixture into an inflatable bag;
        wherein the inflatable bag is an inflatable packaging pillow with a resealable valve;
    (b) inserting a suitable gas into a headspace of the inflatable bag; and (c) permitting sufficient time for an oxidation reaction to proceed,
wherein an incubator shaker is attached to the inflatable bag to provide rotation or rocking of the inflatable bag while the reaction proceeds.

* * * * *